United States Patent [19]

Boller et al.

[11] 4,391,731
[45] Jul. 5, 1983

[54] HYDROGENATED NAPHTHALENES

[75] Inventors: Arthur Boller, Binningen; Martin Schadt, Seltisberg; Alois Villiger, Basel, all of Switzerland

[73] Assignee: Hoffmann-La Roche Inc., Nutley, N.J.

[21] Appl. No.: 289,676

[22] Filed: Aug. 3, 1981

[30] Foreign Application Priority Data

Aug. 14, 1980 [CH] Switzerland ............ 6130/80
May 27, 1981 [CH] Switzerland ............ 3482/81

[51] Int. Cl.³ .................. C09K 3/34; C07C 69/753; C07C 121/46
[52] U.S. Cl. .................. 252/299.62; 260/455 R; 260/465 R; 260/465 D; 260/465 F; 560/8; 560/56; 560/119
[58] Field of Search ........... 260/465 R, 465 F, 465 D, 260/455 R; 560/8, 56, 119; 252/299.62

[56] References Cited

U.S. PATENT DOCUMENTS 3,925,237 12/1975 Ross ..................... 252/299
4,119,558 10/1978 Coates et al. ............... 252/299
4,214,093 7/1980 Fujii et al. ................. 260/465 D X

FOREIGN PATENT DOCUMENTS 56-46855 4/1981 Japan .
56-57754 5/1981 Japan .

OTHER PUBLICATIONS

Coates et al., Mol. Cryst. Liq. Cryst., vol. 41, pp. 119–124, (1978).
Coates et al., Mol. Cryst. Liq. Cryst., vol. 37, pp. 249–262, (1976).
Raramyshiva et al., Chemical Abstracts, vol. 86, 63874j, (1977).

Coates et al., Chemical Abstracts, vo. 89, 42123k, (1978).

Primary Examiner—Dolph H. Torrence
Attorney, Agent, or Firm—Jon S. Saxe; Bernard S. Leon; William G. Isgro

[57] ABSTRACT

Compounds of the formula

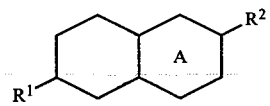

wherein ring A is saturated or aromatic and a saturated ring A which may be present is trans-linked with the second ring; $R^1$ is a straight-chain alkyl or alkoxy group containing 1 to 11 carbon atoms; $R^2$ is cyano, a straight-chain alkyl group containing 1 to 11 carbon atoms, an ester group of the formula

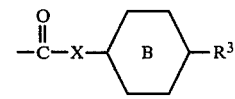

or, when ring A is saturated, additionally a straight-chain alkoxy group containing 1 to 11 carbon atoms; in the ester group of formula II ring B is either aromatic and X is oxygen or sulfur and $R^3$ is cyano or a straight-chain alkyl or alkoxy group containing 1 to 10 carbon atoms, or ring B is a trans-1,4-disubstituted cyclohexane ring and X is oxygen and $R^3$ is cyano or a straight-chain alkyl group containing 1 to 10 carbon atoms; and the total number of carbon atoms in the alkyl and/or alkoxy groups amounts to at most 12, are described. The compounds of formula I are useful in liquid crystal mixtures.

15 Claims, No Drawings

4,391,731

HYDROGENATED NAPHTHALENES

BRIEF SUMMARY OF THE INVENTION

The invention relates to compounds of the formula

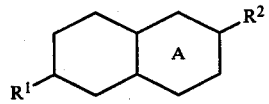

wherein ring A is saturated or aromatic and a saturated ring A which may be present is trans-linked with the second ring; $R^1$ is straight-chain alkyl or alkoxy containing 1 to 11 carbon atoms; $R^2$ is cyano, straight-chain alkyl containing 1 to 11 carbon atoms, an ester group of the formula

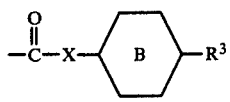

or, when ring A is saturated, additionally straight-chain alkoxy containing 1 to 11 carbon atoms; in the ester group of formula II ring B is either aromatic and X is oxygen or sulfur and $R^3$ is cyano or straight-chain alkyl or alkoxy containing 1 to 10 carbon atoms, or ring B is trans-1,4-disubstituted cyclohexane and X is oxygen and $R^3$ is cyano or straight-chain alkyl containing 1 to 10 carbon atoms; and the total number of carbon atoms in the alkyl and/or alkoxy groups comprises at most 12.

The compounds of formula I are especially valuable as components in liquid crystal mixtures.

In another aspect, the invention relates to intermediates of the formula

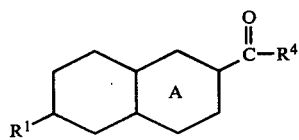

wherein ring A is saturated or aromatic and a saturated ring A which may be present is trans-linked with the second ring, $R^1$ is a straight-chain alkyl or alkoxy group containing 1 to 11 carbon atoms and $R^4$ is hydrogen, chlorine, the hydroxy or amino group or a straight-chain alkyl group containing 1 to 10 carbon atoms.

In yet another aspect, the invention relates to liquid crystal mixtures containing one or more compounds of formula I.

In still another aspect, the invention relates to the use of the compounds of formula I in electro-optical devices.

DETAILED DESCRIPTION OF THE INVENTION

The invention relates to hydrogenated naphthalenes of the formula

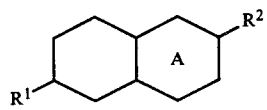

wherein ring A is saturated or aromatic and a saturated ring A which may be present is trans-linked with the second ring; $R^1$ is straight-chain alkyl or alkoxy containing 1 to 11 carbon atoms; $R^2$ is cyano, straight-chain alkyl containing 1 to 11 carbon atoms, an ester group of the formula

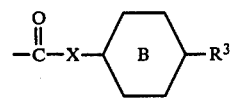

or, when ring A is saturated, additionally a straight-chain alkoxy containing 1 to 11 carbon atoms; in the ester group of formula II ring B is either aromatic and X is oxygen or sulfur and $R^3$ is cyano or straight-chain alkyl or alkoxy containing 1 to 10 carbon atoms, or ring B is trans-1,4-disubstituted cyclohexane ring and X is oxygen and $R^3$ is cyano or straight-chain alkyl containing 1 to 10 carbon atoms; and the total number of carbon atoms in the alkyl and/or alkoxy groups comprises at most 12.

The invention is also concerned with the preparation of the compounds of formula I, liquid crystalline mixtures containing these compounds as well as their use in electro-optical devices.

As used herein, the expression "straight-chain alkyl" denotes, depending on the number of carbon atoms given, methyl, ethyl, propyl, butyl, pentyl, hexyl, heptyl, octyl, nonyl, decyl and undecyl and the expression "straight-chain alkoxy" denotes correspondingly methoxy, ethoxy, propyloxy, butyloxy, pentyloxy, hexyloxy, heptyloxy, octyloxy, nonyloxy, decyloxy and undecyloxy.

The compounds of the invention are especially valuable as components in liquid crystalline mixtures. The compounds of formula I wherein $R^2$ is an ester group of formula II are to a large extent themselves liquid crystalline. The other compounds of formula I, that is, those wherein $R^2$ is cyano or straight-chain alkyl or alkoxy, are suitable above all as doping agents in liquid crystal mixtures.

Those compounds of formula I which contain a cyano group exhibit a high positive anisotropy of the dielectric constants ($\epsilon_{||} > \epsilon_{\perp}$, $\epsilon_{||}$ signifying the dielectric constant along the longitudinal axis of the molecule and $\epsilon_{\perp}$ signifying the dielectric constant perpendicular thereto). On the other hand, the compounds of formula I wherein $R^2$ or $R^3$ is alkyl have only a small anisotropy of the dielectric constants.

In an electric field, liquid crystalline compounds and mixtures which possess a positive anisotropy of the dielectric constants orientate themselves with the direction of their largest dielectric constants parallel to the field direction. This effect is used, inter alia, in the interaction between embedded molecules and the liquid crystalline molecules, guest-host interation, described by J. H. Heilmeier and L. A. Zanoni [Applied Physics Letters 13, 91 (1968)]. Another interesting application of the dielectric field orientation lies in the rotation cell discovered by M. Schadt and W. Helfrich [Applied Physics Letters 18, (1971)] as well as in the Kerr cell described in Molecular Crystals and Liquid Crystals 17, 355 (1972).

These electro-optical rotation cells comprise essentially a condenser with transparent electrodes, the dielectric of which is formed from a nematic crystal with $\epsilon_\parallel > \epsilon_\perp$. The longitudinal molecular axis of the liquid crystal are arranged in twisted form between the condenser plates in the fieldless state. The twisting structure is determined by the given wall orientation of the molecules. After the application of an electric potential to the condenser plates, the molecules adjust themselves with their longitudinal axis in the field direction, that is, perpendicular to the surface of the plates, whereby linear polarized light is no longer rotated in the dielectric, that is, the liquid crystal is uniaxially perpendicular to the surface of the plates. This effect is reversible and can be used to electrically control the optical transmissivity of the condenser.

Since the compounds provided by the invention exhibit different anisotropy of the dielectric constants depending on the nature of the substituents, they can, in addition, be used to adjust the threshold potential of mixtures of the electro-optical cells which are used.

It has also been found that the compounds of formula I wherein $R^2$ is an ester of formula II exhibit a particularly large nematic mesophase range, especially compared with known esters having similar low melting points. Moreover, they have a good chemical stability, low viscosity, ready orientability and slight smectic tendencies, and they give a high contrast in indicating devices.

The compounds of formula I wherein $R^2$ is cyano, alkyl or alkoxy have excellent chemical stability and low viscosity. They are therefore especially suitable for improving the viscosity and, consequently, also the electro-optical operating time of liquid crystalline mixtures. Moreover, the high boiling points of these compounds, compared with previous customary doping agents, facilitate the precise preparation of mixtures in pre-determined ratios, since in this case the evaporation can be held at a very low level.

The compounds in accordance with the invention are colorless and exhibit a high UV stability, since they absorb at short wavelengths and, moreover, with small extinctions. The optical anisotropy differs according to molecular structure; in general, it is greater the larger the unsaturated part of the molecule. Accordingly, by suitable choice of compounds provided by the invention the optical anisotropy of mixtures can be varied, that is, their contrast can be optimized in a given cell.

Further, the compounds provided by the invention have good miscibility with all known liquid crystals.

The compounds of formula I of the invention are either trans-decalins of the formula

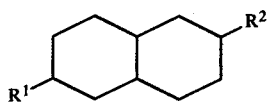

IA or tetralins, that is, 1,2,3,4-tetrahydronaphthalenes, of the formula

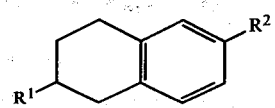

IB wherein $R^1$ and $R^2$ are as previously described.

The compounds of the invention contain at least one chiral center and can therefore be present in optically active or racemic form.

Unless expressly indicated otherwise, the compounds of formula I named hereinafter are, however, generally present as racemates, namely, the compounds of formula IA as the racemate consisting of the compounds of the formulas

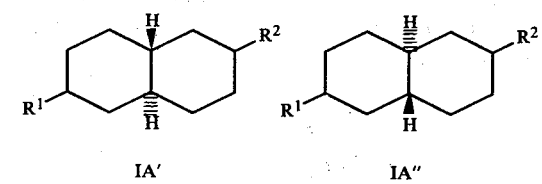

IA'    IA'' and the compounds of formula IB as the racemate consisting of the compounds of the formulas

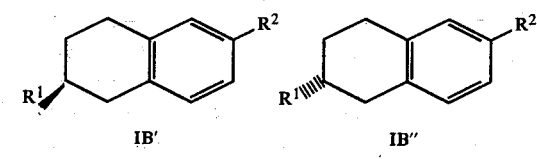

IB'    IB''

The symbol (—) signifies that the corresponding bond to the substituent is directed upwards, that is, above the plane of the drawing; β-position, and the symbol ( ⫼ ) signifies that the corresponding bond to the substituent is directed downwards, that is, below the plane of the drawing; α-position.

In the present invention the representation analogous to formulas I, IA and IB has also been used for the remaining decalins and tetralins.

On the basis of the $^1$H-NMR spectrum of several compounds prepared in accordance with the invention it is assumed that the substituent $R^2$ in the compounds of formula IA stands in the equatorial position. The position of the substituent $R^1$ can not be clarified. On the basis of the pronounced liquid crystalline properties of the decalin esters it is, however, presumed that the substituent $R^1$ also stands in the equatorial position. If this presumption is correct, the compounds of formula IA would be racemates consisting of the compounds of formulas

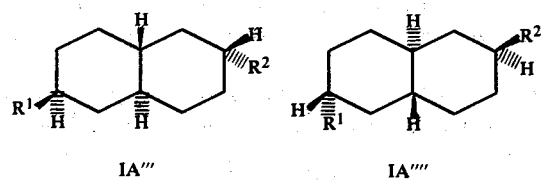

IA'''    IA'''' wherein $R^1$ and $R^2$ are as previously described. However, the compounds of formula IA wherein $R^1$ and $R^2$ are the same are as previously described are an exception, since in this case both of the foregoing formulas are identical and correspond to an optically inactive form.

Of the compounds included within formula I the racemic compounds are preferred.

Moreover, of the compounds of formulas IA and IB those of formula IA are preferred. Further, of the compounds of formula I, preferred are those wherein $R^2$ is an ester of formula II. Preferred ester groups of formula II are those wherein ring B is aromatic and those wherein X is oxygen, preferred $R^3$ groups are cyano and alkyl, especially cyano. Especially preferred liquid crystal components are accordingly the trans-decalin-2-carboxylic acid phenyl esters and especially trans-decalin-2-carboxylic acid p-cyanophenyl ester. Preferred doping agents are those compounds of formula I wherein $R^2$ is cyano or alkyl, especially cyano. Preferred groups denoted by $R^1$ in the compounds of formula I are alkyl. Preferred alkyl and alkoxy groups denoted by $R^1$ or $R^2$ are those containing 1 to 8 carbon atoms, especially those containing 3 to 7 carbon atoms. Of the alkyl and alkoxy groups denoted by $R^3$ in the ester group of formula II, preferred are those containing 1 to 7 carbon atoms, especially those containing 1 to 5 carbon atoms.

The following are examples of preferred compounds of formula I:

6-Methyl-trans-decalin-2-carboxylic acid p-cyanophenyl ester,
6-ethyl-trans-decalin-2-carboxylic acid p-cyanophenyl ester,
6-propyl-trans-decalin-2-carboxylic acid p-cyanophenyl ester,
6-butyl-trans-decalin-2-carboxylic acid p-cyanophenyl ester,
6-pentyl-trans-decalin-2-carboxylic acid p-cyanophenyl ester,
6-hexyl-trans-decalin-2-carboxylic acid p-cyanophenyl ester,
6-heptyl-trans-decalin-2-carboxylic acid p-cyanophenyl ester,
6-octyl-trans-decalin-2-carboxylic acid p-cyanophenyl ester,
6-methyl-trans-decalin-2-carboxylic acid p-butylphenyl ester,
6-ethyl-trans-decalin-2-carboxylic acid p-ethylphenyl ester,
6-propyl-trans-decalin-2-carboxylic acid p-methylphenyl ester,
6-butyl-trans-decalin-2-carboxylic acid p-methylphenyl ester,
6-pentyl-trans-decalin-2-carboxylic acid p-methylphenyl ester,
6-hexyl-trans-decalin-2-carboxylic acid p-methylphenyl ester,
6-heptyl-trans-decalin-2-carboxylic acid p-methylphenyl ester,
6-propyl-trans-decalin-2-carboxylic acid p-ethylphenyl ester,
6-butyl-trans-decalin-2-carboxylic acid p-ethylphenyl ester,
6-pentyl-trans-decalin-2-carboxylic acid p-ethylphenyl ester,
6-hexyl-trans-decalin-2-carboxylic acid p-ethylphenyl ester,
6-heptyl-trans-decalin-2-carboxylic acid p-ethylphenyl ester,
6-propyl-trans-decalin-2-carboxylic acid p-propylphenyl ester,
6-butyl-trans-decalin-2-carboxylic acid p-propylphenyl ester,
6-pentyl-trans-decalin-2-carboxylic acid p-propylphenyl ester,
6-hexyl-trans-decalin-2-carboxylic acid p-propylphenyl ester,
6-heptyl-trans-decalin-2-carboxylic acid p-propylphenyl ester,
6-propyl-trans-decalin-2-carboxylic acid p-butylphenyl ester,
6-butyl-trans-decalin-2-carboxylic acid p-butylphenyl ester,
6-pentyl-trans-decalin-2-carboxylic acid p-butylphenyl ester,
6-hexyl-trans-decalin-2-carboxylic acid p-butylphenyl ester,
6-heptyl-trans-decalin-2-carboxylic acid p-butylphenyl ester,
6-propyl-trans-decalin-2-carboxylic acid p-pentylphenyl ester,
6-butyl-trans-decalin-2-carboxylic acid p-pentylphenyl ester,
6-pentyl-trans-decalin-2-carboxylic acid p-pentylphenyl ester,
6-hexyl-trans-decalin-2-carboxylic acid p-pentylphenyl ester,
6-heptyl-trans-decalin-2-carboxylic acid p-pentylphenyl ester,
6-propyl-trans-decalin-2-carboxylic acid p-methoxyphenyl ester,
6-pentyl-trans-decalin-2-carboxylic acid p-methoxyphenyl ester,
6-heptyl-trans-decalin-2-carboxylic acid p-methoxyphenyl ester,
6-propyl-trans-decalin-2-carboxylic acid p-ethoxyphenyl ester,
6-pentyl-trans-decalin-2-carboxylic acid p-ethoxyphenyl ester,
6-heptyl-trans-decalin-2-carboxylic acid p-ethoxyphenyl ester,
6-propyl-trans-decalin-2-carboxylic acid p-propyloxyphenyl ester,
6-pentyl-trans-decalin-2-carboxylic acid p-propyloxyphenyl ester,
6-heptyl-trans-decalin-2-carboxylic acid p-propyloxyphenyl ester,
6-propyl-trans-decalin-2-carboxylic acid p-pentyloxyphenyl ester,
6-pentyl-trans-decalin-2-carboxylic acid p-pentyloxyphenyl ester,
6-methoxy-trans-decalin-2-carboxylic acid p-cyanophenyl ester,
6-ethoxy-trans-decalin-2-carboxylic acid p-cyanophenyl ester,
6-propyloxy-trans-decalin-2-carboxylic acid p-cyanophenyl ester,
6-butyloxy-trans-decalin-2-carboxylic acid p-cyanophenyl ester,
6-pentyloxy-trans-decalin-2-carboxylic acid p-cyanophenyl ester,
6-hexyloxy-trans-decalin-2-carboxylic acid p-cyanophenyl ester,
6-heptyloxy-trans-decalin-2-carboxylic acid p-cyanophenyl ester,
6-octyloxy-trans-decalin-2-carboxylic acid p-cyanophenyl ester, 6-propyloxy-trans-decalin-2-carboxylic acid p-methylphenyl ester,
6-pentyloxy-trans-decalin-2-carboxylic acid p-methylphenyl ester,
6-heptyloxy-trans-decalin-2-carboxylic acid p-methylphenyl ester,
6-propyloxy-trans-decalin-2-carboxylic acid p-propylphenyl ester,
6-pentyloxy-trans-decalin-2-carboxylic acid p-propylphenyl ester,
6-heptyloxy-trans-decalin-2-carboxylic acid p-propylphenyl ester,
6-propyloxy-trans-decalin-2-carboxylic acid p-pentylphenyl ester,
6-pentyloxy-trans-decalin-2-carboxylic acid p-pentylphenyl ester,
6-heptyloxy-trans-decalin-2-carboxylic acid p-pentylphenyl ester,
6-propyl-trans-decalin-2-carboxylic acid p-cyanophenyl thioester,
6-butyl-trans-decalin-2-carboxylic acid p-cyanophenyl thioester,
6-pentyl-trans-decalin-2-carboxylic acid p-cyanophenyl thioester,
6-hexyl-trans-decalin-2-carboxylic acid p-cyanophenyl thioester,
6-heptyl-trans-decalin-2-carboxylic acid p-cyanophenyl thioester,
6-propyl-trans-decalin-2-carboxylic acid trans-4-cyano-1-cyclohexyl ester,
6-butyl-trans-decalin-2-carboxylic acid trans-4-cyano-1-cyclohexyl ester,
6-pentyl-trans-decalin-2-carboxylic acid trans-4-cyano-1-cyclohexyl ester,
6-hexyl-trans-decalin-2-carboxylic acid trans-4-cyano-1-cyclohexyl ester,
6-heptyl-trans-decalin-2-carboxylic acid trans-4-cyano-1-cyclohexyl ester,
6-propyl-trans-decalin-2-carboxylic acid trans-4-methyl-1-cyclohexyl ester,
6-pentyl-trans-decalin-2-carboxylic acid trans-4-methyl-1-cyclohexyl ester,
6-heptyl-trans-decalin-2-carboxylic acid trans-4-methyl-1-cyclohexyl ester,
6-propyl-trans-decalin-2-carboxylic acid trans-4-propyl-1-cyclohexyl ester,
6-pentyl-trans-decalin-2-carboxylic acid trans-4-propyl-1-cyclohexyl ester,
6-heptyl-trans-decalin-2-carboxylic acid trans-4-propyl-1-cyclohexyl ester,
6-propyl-trans-decalin-2-carboxylic acid trans-4-pentyl-1-cyclohexyl ester,
6-butyl-trans-decalin-2-carboxylic acid trans-4-pentyl-1-cyclohexyl ester,
6-pentyl-trans-decalin-2-carboxylic acid trans-4-pentyl-1-cyclohexyl ester,
6-heptyl-trans-decalin-2-carboxylic acid trans-4-pentyl-1-cyclohexyl ester,
6-ethyl-trans-decalin-2-carbonitrile,
6-propyl-trans-decalin-2-carbonitrile,
6-pentyl-trans-decalin-2-carbonitrile,
6-heptyl-trans-decalin-2-carbonitrile,
6-pentyloxy-trans-decalin-2-carbonitrile,
2-ethyl-6-propyl-trans-decalin,
2-ethyl-6-pentyl-trans-decalin,
2-ethyl-6-heptyl-trans-decalin,
2,6-dipropyl-trans-decalin,
2-butyl-6-propyl-trans-decalin,
2-pentyl-6-propyl-trans-decalin,
2-pentyl-6-butyl-trans-decalin,
2,6-dipentyl-trans-decalin,
2-hexyl-6-propyl-trans-decalin,
2-hexyl-6-pentyl-trans-decalin,
2-heptyl-6-propyl-trans-decalin,
2-heptyl-6-butyl-trans-decalin,
2-heptyl-6-pentyl-trans-decalin,
2-propyloxy-6-propyl-trans-decalin,
2-propyloxy-6-pentyl-trans-decalin,
2-propyloxy-6-heptyl-trans-decalin,
2-pentyloxy-6-propyl-trans-decalin,
2-pentyloxy-6-pentyl-trans-decalin,
2-pentyloxy-6-heptyl-trans-decalin,
2-heptyloxy-6-propyl-trans-decalin,
p-cyanophenyl 2-methyl-1,2,3,4-tetrahydro-6-naphthoate,
p-cyanophenyl 2-ethyl-1,2,3,4-tetrahydro-6-naphthoate,
p-cyanophenyl 2-propyl-1,2,3,4-tetrahydro-6-naphthoate,
p-cyanophenyl 2-butyl-1,2,3,4-tetrahydro-6-naphthoate,
p-cyanophenyl 2-pentyl-1,2,3,4-tetrahydro-6-naphthoate,
p-cyanophenyl 2-hexyl-1,2,3,4-tetrahydro-6-naphthoate,
p-cyanophenyl 2-heptyl-1,2,3,4-tetrahydro-6-naphthoate,
p-cyanophenyl 2-octyl-1,2,3,4-tetrahydro-6-naphthoate,
p-methylphenyl 2-propyl-1,2,3,4-tetrahydro-6-naphthoate,
p-methylphenyl 2-pentyl-1,2,3,4-tetrahydro-6-naphthoate,
p-methylphenyl 2-heptyl-1,2,3,4-tetrahydro-6-naphthoate,
p-propylphenyl 2-propyl-1,2,3,4-tetrahydro-6-naphthoate,
p-propylphenyl 2-pentyl-1,2,3,4-tetrahydro-6-naphthoate,
p-propylphenyl 2-heptyl-1,2,3,4-tetrahydro-6-naphthoate,
p-butylphenyl 2-pentyl-1,2,3,4-tetrahydro-6-naphthoate,
p-pentylphenyl 2-propyl-1,2,3,4-tetrahydro-6-naphthoate,
p-pentylphenyl 2-pentyl-1,2,3,4-tetrahydro-6-naphthoate,
p-pentylphenyl 2-heptyl-1,2,3,4-tetrahydro-6-naphthoate,
p-cyanophenyl 2-propyloxy-1,2,3,4-tetrahydro-6-naphthoate,
p-cyanophenyl 2-pentyloxy-1,2,3,4-tetrahydro-6-naphthoate,
p-cyanophenyl 2-heptyloxy-1,2,3,4-tetrahydro-6-naphthoate,
p-methylphenyl 2-pentyloxy-1,2,3,4-tetrahydro-6-naphthoate,
p-propylphenyl 2-pentyloxy-1,2,3,4-tetrahydro-6-naphthoate,
p-pentylphenyl 2-pentyloxy-1,2,3,4-tetrahydro-6-naphthoate,
p-methoxyphenyl 2-pentyl-1,2,3,4-tetrahydro-6-naphthoate,
p-ethoxyphenyl 2-pentyl-1,2,3,4-tetrahydro-6-naphthoate,
p-propyloxyphenyl 2-pentyl-1,2,3,4-tetrahydro-6-naphthoate, p-ethoxyphenyl 2-heptyl-1,2,3,4-tetrahydro-6-naphthoate,
S-(p-cyanophenyl) 2-propyl-1,2,3,4-tetrahydro-thio-6-naphthoate,
S-(p-cyanophenyl) 2-butyl-1,2,3,4-tetrahydro-thio-6-naphthoate,
S-(p-cyanophenyl) 2-pentyl-1,2,3,4-tetrahydro-thio-6-naphthoate,
S-(p-cyanophenyl) 2-hexyl-1,2,3,4-tetrahydro-thio-6-naphthoate,
S-(p-cyanophenyl) 2-heptyl-1,2,3,4-tetrahydro-thio-6-naphthoate,
S-(p-ethoxyphenyl) 2-pentyl-1,2,3,4-tetrahydro-thio-6-naphthoate,
(trans-4-cyano-1-cyclohexyl) 2-propyl-1,2,3,4-tetrahydro-6-naphthoate,
(trans-4-cyano-1-cyclohexyl) 2-butyl-1,2,3,4-tetrahydro-6-naphthoate,
(trans-4-cyano-1-cyclohexyl) 2-pentyl-1,2,3,4-tetrahydro-6-naphthoate,
(trans-4-cyano-1-cyclohexyl) 2-hexyl-1,2,3,4-tetrahydro-6-naphthoate,
(trans-4-cyano-1-cyclohexyl) 2-heptyl-1,2,3,4-tetrahydro-6-naphthoate,
(trans-4-methyl-1-cyclohexyl) 2-propyl-1,2,3,4-tetrahydro-6-naphthoate,
(trans-4-methyl-1-cyclohexyl) 2-pentyl-1,2,3,4-tetrahydro-6-naphthoate,
(trans-4-methyl-1-cyclohexyl) 2-heptyl-1,2,3,4-tetrahydro-6-naphthoate,
(trans-4-propyl-1-cyclohexyl) 2-propyl-1,2,3,4-tetrahydro-6-naphthoate,
(trans-4-propyl-1-cyclohexyl) 2-pentyl-1,2,3,4-tetrahydro-6-naphthoate,
(trans-4-propyl-1-cyclohexyl) 2-heptyl-1,2,3,4-tetrahydro-6-naphthoate,
2-propyl-1,2,3,4-tetrahydro-6-naphthonitrile,
2-pentyl-1,2,3,4-tetrahydro-6-naphthonitrile,
2-heptyl-1,2,3,4-tetrahydro-6-naphthonitrile,
2-pentyloxy-1,2,3,4-tetrahydro-6-naphthonitrile,
2,6-dipropyl-1,2,3,4-tetrahydro-6-naphthalene,
2-propyl-6-pentyl-1,2,3,4-tetrahydro-6-naphthalene,
2-propyl-6-heptyl-1,2,3,4-tetrahydro-6-naphthalene,
2-pentyl-6-propyl-1,2,3,4-tetrahydro-6-naphthalene,
2,6-dipentyl-1,2,3,4-tetrahydro-6-naphthalene,
2-pentyl-6-heptyl-1,2,3,4-tetrahydro-6-naphthalene,
2-heptyl-6-propyl-1,2,3,4-tetrahydro-6-naphthalene,
2-heptyl-6-pentyl-1,2,3,4-tetrahydro-6-naphthalene,
2-propyloxy-6-pentyl-1,2,3,4-tetrahydro-6-naphthalene,
2-pentyloxy-6-pentyl-1,2,3,4-tetrahydro-6-naphthalene.

The compounds of formula I can be prepared in accordance with the invention by (a) for the preparation of the compounds of formula I wherein $R^2$ is an ester of formula II, esterifying a compound of the formula

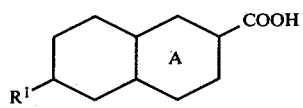

wherein $R^1$ and A are as previously described, or a reactive derivative thereof with a compound of the formula

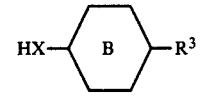

wherein X, B and $R^3$ are as previously described, or a suitable salt thereof, or (b) for the preparation of the compounds of formula I wherein $R^2$ is cyano, dehydrating a compound of the formula

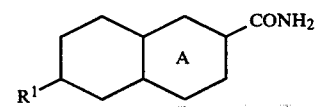

wherein $R^1$ and A are as previously described, or (c) for the preparation of the compounds of formula I wherein $R^2$ is straight-chain alkyl containing 1 to 11 carbon atoms, reacting a compound of the formula

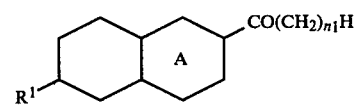

wherein $n_1$ is an integer of 0 to 10 and $R^1$ and A are as previously described, with hydrazine in the presence of a base, or (d) for the preparation of the compounds of formula I wherein $R^2$ is straight-chain alkyl containing 2 to 11 carbon atoms, catalytically hydrogenating a compound of the formula

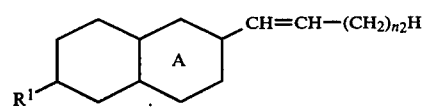

wherein $n_2$ is an integer of 0 to 9 and $R^1$ and A are as previously described, or (e) for the preparation of the compounds of formula I wherein ring A is saturated and $R^2$ is straight-chain alkoxy, etherifying a compound of the formula

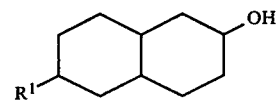

wherein $R^1$ is as previously described.

The esterification of a compound of formula III or a reactive derivative thereof, for example an anhydride or acid halide, with a compound of formula IV or a suitable salt thereof, for example the sodium salt, can be carried out in a known manner. The reaction of an acid of formula III with a compound of formula IV is conveniently carried out in the presence of a catalytic amount of an acid, for example sulfuric acid or a hydrohalic acid, in the presence or absence of an inert organic solvent. It can, however, also be carried out in the presence of N,N'-dicyclohexyl-carbodiimide and 4-(dimethylamino)pyridine. The preferred method, however, comprises reacting the acid chloride, the compound of formula IX in Scheme 3, of a compound of formula III with a compound of formula IV. This reaction is conveniently carried out in an inert organic solvent, for example an ether such as diethyl ether or tetrahydrofuran, dimethylformamide, benzene, toluene, cyclohexane, carbon tetrachloride and the like. In order to bind the hydrogen chloride which is liberated during the reaction, there is conveniently used an acid-binding agent, for example a tertiary amine, pyridine and the like. Preferably, the acid-binding agent is used in a large excess so that it can simultaneously serve as the solvent. The temperature and pressure are not critical and the reaction is generally carried out at atmospheric pressure and at a temperature in the range of room temperature to the boiling point of the reaction mixture.

The dehydration of a compound of formula V can be carried out using any suitable dehydrating agent such as, for example, with phosphorus oxychloride, phosphorus pentoxide, thionyl chloride, acetic anhydride or, especially, benzenesulfonyl chloride and the like. The dehydration can be carried out in an inert organic solvent such as, for example, a hydrocarbon or halogenated hydrocarbon, and, if desired, in the presence of a base such as sodium acetate, pyridine or triethylamine. It can, however, also be carried out in the absence of an organic solvent. The reaction is preferably carried out at a temperature in the range of about 50° C. to the reflux temperature of the reaction mixture. The pressure is not critical and the reaction is advantageously carried out at atmospheric pressure.

The reaction of a compound of formula VI with hydrazine in the presence of a base, for example potassium hydroxide, sodium ethylate, potassium tert-butylate and the like, is conveniently carried out in an inert organic solvent such as dimethyl sulfoxide or an alcohol, for example ethanol, diethyleneglycol or triethyleneglycol and the like. The hydrazone formed is generally decomposed only at an elevated temperature, for example about 200° C. If, however, dimethyl sulfoxide is used as the solvent, then the decomposition frequently already takes place at room temperature. If the decomposition temperature lies above the boiling point of the reaction mixture, then it is necessary to work under elevated pressure. The preferred method comprises carrying out the reaction according to the Huang-Minlon process, that is, heating a ketone of formula VI under reflux in a water-miscible high-boiling solvent, for example diethyleneglycol or triethyleneglycol, together with hydrazine hydrate and potassium hydroxide, subsequently distilling the water up to the decomposition of the hydrazone and then boiling the mixture under reflux until the reduction is complete.

The catalytic hydrogenation of a compound of formula VII can be carried out using any customary hydrogenation catalyst such as palladium, platinum, Raney-nickel and the like, if desired on an inert carrier material. Palladium and platinum are preferred catalysts. The solvent used can be any inert organic solvent such as a saturated alcohol, ether, ester, carboxylic acid and the like; for example, ethanol, dioxane, ethyl acetate or glacial acetic acid. Conveniently, the catalytic hydrogenation is carried out with the addition of a base such as triethylamine or 4-(dimethylamino)pyridine. The temperature and pressure at which the catalytic hydrogenation is carried out are not critical. Conveniently, the catalytic hydrogenation is carried out at a temperature in the range of room temperature to the boiling point of the mixture and a pressure of about 1 to about 5 atmospheres.

For the etherification of a compound of formula VIII, a corresponding alcoholate, for example, the sodium alcoholate, is conveniently reacted with a corresponding alkyl halide, preferably an alkyl bromide or iodide. The alcoholate can be obtained in a known manner; for example, by reacting the alcohol with an alkali metal or alkali metal hydride. The etherification is conveniently carried out in an inert organic solvent, for example, a hydrocarbon or ether. A preferred embodiment comprises reacting an alcohol of formula VIII with sodium hydride and an alkyl bromide or iodide in monoglyme, if desired in the presence of sodium iodide. The temperature and pressure are not critical. However, the reaction is preferably carried out at atmospheric pressure and room temperature.

The compounds of formula IV are known compounds or are analogues of known compounds. The compounds of formulas III and V–IX also form part of the present invention. The acids of formula III have for the most part liquid crystalline properties. The compounds of formulas III, V, VI and IX can be grouped together by the formula

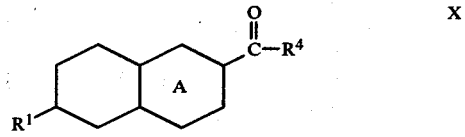

wherein $R^1$ and A are as previously described and $R^4$ is hydrogen, chlorine, hydroxy, amino or straight-chain alkyl containing 1 to 10 carbon atoms.

The compounds of formulas III and V–IX can be prepared according to Reaction Schemes 1–3 which follow, wherein $R^1$, A, $n_1$ and $n_2$ are as previously described, $n_3$ is an integer of 1 to 10, the symbol ($\sim$) indicates that the substituent in question can stand in the α- or β-position, that is, below or above the plane of the formula, and the dotted line (- - -) indicates that one of the bonds denoted thereby is a double bond.

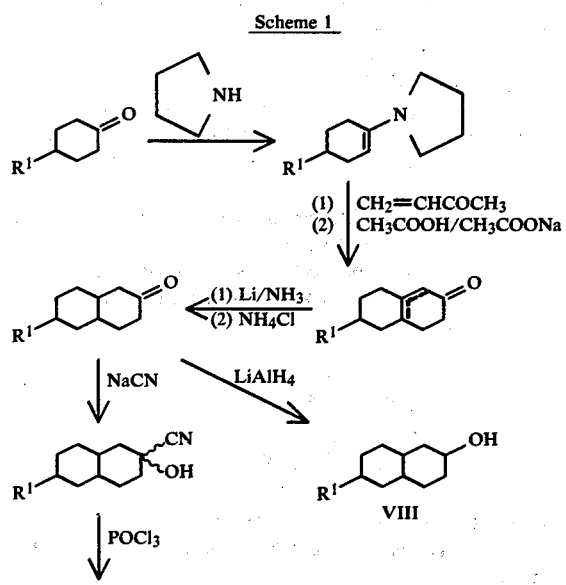

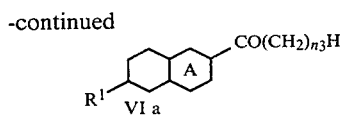

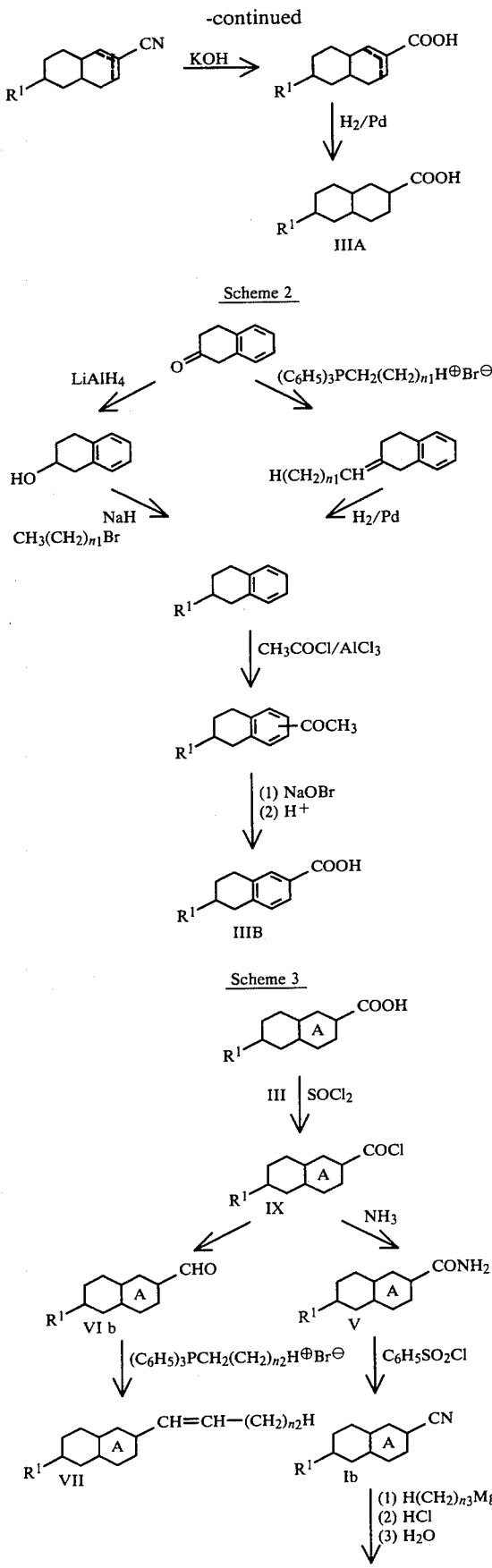

The reaction of a cyclohexanone with pyrrolidine, in accordance with Scheme 1, can be carried out, for example, in toluene using a catalytic amount of p-toluenesulfonic acid. The water which is formed is conveniently separated by means of a water-separator.

The reaction of the 1-pyrrolidinyl-1-cyclohexene with methyl vinyl ketone is carried out most suitably in absolute toluene and in an inert gas atmosphere by adding dropwise the methyl vinyl ketone and, after several hours, heating the mixture to reflux while adding dropwise a sodium acetate/acetic acid solution. There is obtained a 6-pentyl-octahydro-$\Delta^{1,9}$-naphthalen-2-one and 6pentyl-octahydro-$\Delta^{9,10}$-naphthalen-2-one, which can be used without separation.

The reduction of the mixture of unsaturated ketones can be carried out, for example, using lithium in liquid ammonia. After adding ammonium chloride and working-up, there is obtained the corresponding trans-decalin-2-one in admixture with the cis-decalin-2-one.

The decalin-2-one mixture, dissolved in an inert organic solvent, for example, ether, can be converted into the corresponding cyanohydrin mixture, for example using a sodium cyanide solution and hydrochloric acid at about 0° C.

The dehydration of the cyanohydrin mixture can be carried out using any suitable dehydrating agent such as phosphorus oxychloride, phosphorus pentoxide and the like in an inert organic solvent or solvent mixture, preferably pyridine, benzene and the like, and heating to reflux. The thus-obtained mixture of octahydro-$\Delta^1$-naphthalene-2-carbonitrile and octahydro-$\Delta^2$-naphthalene-2-carbonitrile can be used without separation.

The saponification of the mixture of unsaturated nitriles can be carried out, for example, using a solution of potassium hydroxide in diethyleneglycol and heating at about 200° C. After acidification and extraction, there is obtained a mixture of the corresponding octahydro-$\Delta^1$-naphthalenecarboxylic acid and octahydro-$\Delta^2$-naphthalene-carboxylic acid.

The catalytic hydrogenation of the unsaturated acids can be carried out using any conventional hydrogenation catalyst such as palladium, platinum, Raney-nickel and the like, if desired on an inert carrier material. The solvent can be a saturated alcohol, ether, ester, carboxylic acid and the like, preferably ethanol. The resulting crude transdecalin-2-carboxylic acid of formula IIIA, which usually still contains cis isomer, can be purified by recrystallization and sublimation in a high vacuum.

The conversion of the aforementioned trans-decalin-2-one, optionally in admixture with the cis isomer, into an alcohol of formula VIII can be carried out, for example, using lithium aluminum hydride in an inert organic solvent such as tetrahydrofuran, diethyl ether and the like. The crude product of formula VIII obtained can be purified by recrystallization and chromatography.

In accordance with Scheme 2,2-tetralone can be converted into the corresponding 2-alkylidene-1,2,3,4-tetrahydronaphthalene, for example by Wittig alkylation with an alkyltriphenylphosphonium bromide. The reaction is conveniently carried out in an inert organic solvent, for example an ether or a saturated or aromatic hydrocarbon such as diethyl ether, tetrahydrofuran, dioxane, dimethoxyethane, toluene and the like, at a temperature in the range of room temperature to the boiling point of the reaction mixture. The base used is preferably an alkali metal alcoholate such as potassium tert-butylate and sodium methylate.

The catalytic hydrogenation of a 2-alkylidene-1,2,3,4-tetrahydronaphthalene can be carried out in an analogous manner to the hydrogenation of a compound of formula VII described earlier.

The reduction of 2-tetralone to the alcohol can be carried out, for example, using lithium aluminum hydride in an inert organic solvent such as tetrahydrofuran, diethyl ether and the like.

The etherification of the alcohol (or an alcoholate) to a 2-alkoxy-1,2,3,4-tetrahydronaphthalene can be carried out in an analogous manner to the etherification of an alcohol of formula VIII described earlier.

The 2-alkyl-1,2,3,4-tetrahydronaphthalenes or 2-alkoxy-1,2,3,4-tetrahydronaphthalenes can be converted in a known manner by Friedel-Crafts acylation, for example using acetyl chloride and aluminum chloride in dichloromethane, and oxidation with sodium hypobromite, preferably in dioxane, into a mixture of the corresponding 1,2,3,4-tetrahydronaphthalene-6-carboxylic acid and 1,2,3,4-tetrahydronaphthalene-7-carboxylic acid. This mixture can be separated by recrystallization; however, the separation of the corresponding amides is simpler.

The carboxylic acids of formula III can be converted into acid chlorides of formula IX in a known manner; for example using thionyl chloride.

The conversion of an acid chloride of formula IX into the corresponding amide of formula V can be carried out, for example, using gaseous ammonia in an inert organic solvent, for example, a halogenated hydrocarbon, such as, dichloromethane.

The dehydration of an amide of formula V to give a nitrile of formula Ib has been described earlier.

The nitriles of formula Ib can be alkylated with a Grignard solution, for example, a solution of the corresponding alkylmagnesium bromide in an ether such as diethyl ether, tetrahydrofuran and the like, and converted, by introducing hydrogen chloride gas, into imine hydrochlorides. These can then be converted into ketones of formula VIa by warming slightly with water.

Further, the aforementioned acid chlorides of formula IX can be converted into aldehydes of formula VIb in a known manner; for example, by Rosenmund reaction with hydrogen and a partially deactivated palladium catalyst in a boiling hydrocarbon.

Finally, the aldehydes of formula VIb can be converted into compounds of formula VII by Wittig alkylation in an analogous manner to the alkylation of 2-tetralone described earlier.

In order to prepare optically active compounds of formula I, the compounds of formula III or VIII are conveniently resolved into the optical antipodes according to racemate resolution methods which are known, for example, via diastereomeric amides or esters, and then further reacted in an analogous manner. For example, the acids of formula IIIA, which have 4 chiral centers, can be reacted with α-phenylethylamine, the diastereomeric amides obtained can be separated and subsequently hydrolyzed to the optically active acids.

The compounds of formula I can be used in the form of mixtures consisting of two or more compounds of formula I or in the form of mixtures with other nematic and/or non-nematic substances such as, for example, with substances from the classes of Schiff's bases, azobenzenes, azoxybenzenes, phenyl benzoates, cyclohexanecarboxylic acid phenyl esters, biphenyls, terphenyls, phenylcyclohexanes, cinnamic acid derivatives, phenylpyrimidines, diphenylpyrimidines, cyclohexylphenylpyrimidines, phenyldioxanes and the like. Such compounds are familiar and known to persons skilled in the art; for example, from German Offenlegungsschriften 2 306 738, 2 306 739, 2 429 093, 2 356 085, 2 636 684, 2 459 374, 2 547 737, 2 641 724, 2 708 276, 2 811 001 and from z. Naturforsch, 34b, 1535 (1979). Many of such nematic or non-namatic substances are, moreover, commercially available. The compounds of formula I wherein $R^2$ is an ester group of formula II can, however, also be used in pure form.

The liquid crystalline mixtures in accordance with the invention must contain at least one compound having liquid crystalline properties in sufficient amount so that the total mixture also has liquid crystalline properties. The weight ratio of the components of the mixture preferably corresponds to the eutectic composition. However, the proportion of the compounds of formula I can generally be chosen arbitrarily (the preferred concentration range is about 1 to about 80 mol precent) when $R^2$ is an ester group and, when $R^2$ is alkyl, alkoxy or cyano, usually amounts in the range of up to about 40 mol percent, preferably in the range of between about 1 to about 30 mol percent.

Further, the compounds provided by the invention can contain optically active compounds, for example optically active biphenyls, and/or dichroic coloring substances, for example, azo, azoxy and anthraquinone coloring substances. The proportion of such compounds is determined by the desired pitch, color, extinction, solubility and the like.

The preparations of mixtures containing, inter alia, compounds of formula I as well as other liquid crystalline and/or non-liquid crystalline compounds and/or dichroic coloring substances can be carried out in a known manner; for example, by heating a mixture of the components to a temperature barely above the clearing point and subsequently cooling down.

The invention is also concerned with all novel compounds, mixtures, processes, uses and devices as herein described.

The Mixture of Examples 1–13 are examples of preferred nematic mixtures. Mixtures of Examples 1–10 illustrate the influence of the compounds provided by the invention when they are added to mixtures of known liquid crystals, that is, basic mixture A–C. $\eta_M/\eta_H$ is the ratio of the viscosity of a mixture ($\eta_M$) to the viscosity of the basic mixture which is used ($\eta_H$).

Basic mixture A 5.77 weight % of p-butylbenzoic acid p'-cyanophenyl ester,
5.19 weight % of p-(5-pentyl-2-pyrimidinyl)benzonitrile,
11.54 weight % of p-(5-heptyl-2-pyrimidinyl)benzonitrile,
12.15 weight % of trans-4-propylcyclohexanecarboxylic acid p'-cyanophenyl ester,
12.37 weight % of trans-4-pentylcyclohexanecarboxylic acid p'-cyanophenyl ester,
22.02 weight % of trans-4-butylcyclohexanecarboxylic acid p-(ethoxy)phenyl ester, 19.92 weight % of trans-4-pentylcyclohexanecarboxylic acid p-(methoxy)phenyl ester,
11.04 weight % of trans-p-[5-(4-ethylcyclohexyl)-2-pyrimidinyl]benzonitrile;
melting point $< -10°$ C.; clearing point 72.7°–73.0° C.

Basic mixture B 8.00 weight % of p-butylbenzoic acid p'-cyanophenyl ester,
7.19 weight % of p-(5-pentyl-2-pyrimidinyl)benzonitrile,
15.00 weight % of p-(5-heptyl-2-pyrimidinyl)benzonitrile,
15.54 weight % of trans-4-propylcyclohexanecarboxylic acid p-cyanophenyl ester,
9.71 weight % of trans-4-butylcyclohexanecarboxylic acid p-cyanophenyl ester,
15.54 weight % of trans-4-pentylcyclohexanecarboxylic acid p-cyanophenyl ester,
12.52 weight % of trans-p-[5-(4-ethylcyclohexyl)-2-pyrimidinyl]benzonitrile,
16.50 weight % of trans-p-[5-(4-heptylcyclohexyl)-2-pyrimidinyl]-benzonitrile;
melting point $< -10°$ C.; clearing point 104.6°–106.8° C.

Basic mixture C 28.34 weight % of 4'-pentyl-4-cyanobiphenyl,
7.94 weight % of trans-4-propylcyclohexanecarboxylic acid p-cyanophenyl ester,
7.22 weight % of trans-4-pentylcyclohexanecarboxylic acid p-cyanophenyl ester,
14.68 weight % of trans-4-butylcyclohexanecarboxylic acid p-(ethoxy)phenyl ester,
13.11 weight % of trans-4-pentylcyclohexanecarboxylic acid p-(methoxy)phenyl ester,
8.03 weight % of trans-p-[5-(4-ethylcyclohexyl)-2-pyrimidinyl]benzonitrile,
5.74 weight % of trans-p-[5-(4-pentylcyclohexyl)-2-pyrimidinyl]benzonitrile,
14.94 weight % of trans-p-[5-(4-heptylcyclohexyl)-2-pyrimidinyl]benzonitrile;
melting point $< -10°$ C.; clearing point 97.5° C.

Mixture Example 1

90.0 weight % of basic mixture A,
10.0 weight % of 6-butyl-trans-decalin-2-carboxylic acid trans-4-pentyl-1-cyclohexyl ester;
melting point $< -10°$ C.; clearing point 75.4°–75.7° C.

Mixture Example 2

87.53 weight % of basic mixture A,
12.47 weight % of 6-pentyl-trans-decalin-2-carboxylic acid p-ethoxyphenyl ester;
melting point $< -10°$ C.; clearing point 80.7°–81.1° C.

Mixture Example 3

87.47 weight % of basic mixture A,
12.53 weight % of p-cyanophenyl-2-heptyl-1,2,3,4-tetrahydro-6-naphthoate;
melting point $< -10°$ C.; clearing point 79.7°–80.2° C.

Mixture Example 4

86.87 weight % of basic mixture A,
13.13 weight % of p-ethoxyphenyl-2-heptyl-1,2,3,4-tetrahydro-6-naphthoate;
melting point $< -10°$ C.; clearing point 78.8°–79.1° C.

Mixture Example 5

87.33 weight % of basic mixture A,
12.67 weight % of p-butylphenyl-2-pentyl-1,2,3,4-tetrahydro-6-naphthoate;
melting point $< -10°$ C.; clearing point 73.3°–73.6° C.

Mixture Example 6

91.73 weight % of basic mixture A,
8.27 weight % of 2-ethyl-6-pentyl-trans-decalin;
melting point $< -10°$ C.; clearing point 61.7°–62.5° C.;
$\eta_M/\eta_H = 0.783$ Mixture Example 7

91.73 weight % of basic mixture C,
8.27 weight % of 2-ethyl-6-pentyl-trans-decalin;
melting point $< -10°$ C.; clearing point 83.4°–86.2° C.;
$\eta_M/\eta_H = 0.80$ Mixture Example 8

91.73 weight % of basic mixture B,
8.27 weight % of 2-ethyl-6-pentyl-trans-decalin;
melting point $< -10°$ C.; clearing point 89.7°–91.9° C.;
$\eta_M/\eta_H = 0.63$ Mixture Example 9

90.80 weight % of basic mixture A,
9.20 weight % of 2-ethyl-6-heptyl-trans-decalin;
melting point $< -10°$ C.; clearing point 62.0°–62.7° C.;
$\eta_M/\eta_H = 0.771$ Mixture Example 10

88.87 weight % of basic mixture A,
11.13 weight % of 6-propyl-trans-decalin-2-carboxylic acid p-ethylphenyl ester;
melting point $< -10°$ C.; clearing point 74.0°–74.4° C.

Mixture Example 11

8.00 weight % of p-butylbenzoic acid p'-cyanophenyl ester,
7.20 weight % of p-(5-pentyl-2-pyrimidinyl)benzonitrile,
16.00 weight % of p-(5-heptyl-2-pyrimidinyl)benzonitrile,
29.07 weight % of trans-4-butylcyclohexenecarboxylic acid p-(ethoxy)phenyl ester,
6.22 weight % of 6-propyl-trans-decalin-2-carboxylic acid p-cyanophenyl ester,
13.62 weight % of 6-pentyl-trans-decalin-2-carboxylic acid p-ethylphenyl ester,
19.89 weight % of 6-butyl-trans-decalin-2-carboxylic acid trans-4-pentyl-1-cyclohexyl ester;
melting point $< -10°$ C.; clearing point 70.4°–70.5° C.

Mixture Example 12

22.97 weight % of 4'-heptyl-4-cyanobiphenyl,
24.24 weight % of trans-4-butylcyclohexanecarboxylic acid p-(ethoxy)phenyl ester,
21.33 weight % of trans-4-pentylcyclohexanecarboxylic acid p-(methoxy)phenyl ester,
5.18 weight % of 6-propyl-trans-decalin-2-carboxylic acid p-cyanophenyl ester,
11.35 weight % of 6-pentyl-trans-decalin-2-carboxylic acid p-ethylphenyl ester,
14.93 weight % of 6-butyl-trans-decalin-2-carboxylic acid trans-4-pentyl-1-cyclohexyl ester;
melting point $< -10°$ C.; clearing point 70.6°–70.7° C.

Mixture Example 13

22.19 weight % of trans-4butylcyclohexanecarboxylic acid p-(ethoxy)phenyl ester,
20.18 weight % of trans-4-pentylcyclohexanecarboxylic acid p-(methoxy)phenyl ester,
29.63 weight % of p-[2-(trans-4-propylcyclohexyl)-1-ethyl]benzonitrile,
4.31 weight % of 6-propyl-trans-decalin-2-carboxylic acid p-cyanophenyl ester,
9.45 weight % of 6-pentyl-trans-decalin-2-carboxylic acid p-ethylphenyl ester,
14.24 weight % of 6-butyl-trans-decalin-2-carboxylic acid trans-4-pentyl-1-cyclohexyl ester;
melting point < −10° C.; clearing point 64.2°–64.3° C.

The preparation of the compounds of formula I of the invention is further illustrated by the Examples which follow.

EXAMPLE 1

Preparation of p-cyanophenyl 2-pentyl-1,2,3,4-tetrahydro-6-naphthoate 6.16 g of 2-pentyl-1,2,3,4-tetrahydronaphthalene-6-carboxylic acid are boiled at reflux with 62.5 ml of thionyl chloride while excluding moisture for 2 hours. After removing the excess thionyl chloride, the acid chloride is obtained as a yellowish oil.

The acid chloride, diluted with 10 ml of absolute benzene, is added dropwise while stirring at 3°–7° C. to a solution, cooled to 3° C., of 2.99 g of p-cyanophenol in 15 ml of absolute pyridine, the mixture is left to stand overnight, then poured into a mixture of 30 g of ice and 30 ml of hydrochloric acid (1:1), exhaustively extracted with ether and the organic hases are washed once with 35 ml of ice-cold 1 N sodium hydroxide and water. After drying with sodium sulfate and removing the solvent in vacuo, there is obtained a crystalline residue (8.6 g) of p-cyanophenyl 2-pentyl-1,2,3,4-tetrahydro-6-naphthoate which, for purification, is chromatographed on 230 g of silica gel. Elution with benzene/hexane (1:1) and benzene yields 8.1 g of substance which is recrystallized from acetone/hexane up to constant melting point and clearing point and dried up to constant weight in a high vacuum (0.01 mbar). There are obtained colorless crystals of p-cyanophenyl 2-pentyl-1,2,3,4-tetrahydro-6-naphthoate; melting point of 72.7°–73.3° C., clearing point of 127.7° C.

The 2-pentyl-1,2,3,4-tetrahydronaphthalene-6-carboxylic acid used as the starting material can be prepared as follows:

(a) 51.6 g of potassium tert-butylate are added to a suspension of 178 g of n-pentyltriphenylphosphonium bromide in 1560 ml of absolute toluene, the mixture is stirred at room temperature for 45 minutes, a solution of 41.9 g of 2-tetralone in 300 ml of absolute toluene is added dropwise thereto with 50 minutes and the mixture is heated at 75°–80° C. for 3 hours. The mixture is left to cool down and poured into 1500 ml of ice/water. The organic phase is separated, the aqueous phase is extracted twice more with toluene and the combined toluene phases are washed with water. After drying over sodium sulfate and removing the solvent in vacuo, there are obtained 175 g of a brownish suspension which, for purification, is filtered through a column of 450 g of silica gel. Elution with hexane and benzene/hexane (1:1) yields 53.2 g of 2-pentylidene-1,2,3,4-tetrahydronaphthalene as a yellowish oil.

(b) A mixture of 53.2 g of 2-pentylidene-1,2,3,4-tetrahydronaphthalene, 275 ml of rectified alcohol, 1.4 ml of triethylamine and 1.44 g of palladium/carbon (5%) is shaken at room temperature in a hydrogen atmosphere until the hydrogenation is complete (24 hours). Subsequently, the catalyst is removed by filtration and the solvent is removed in vacuo. The 49.4 g of 2-pentyl-1,2,3,4-tetrahydronaphthalene remaining as the residue are purified by distillation in a high vacuum; 47.3 g of a colorless liquid; boiling point of 106°–110° C. (0.5 mbar).

(c) 37.6 g of anhydrous aluminum chloride are added portionwise while stirring at room temperature within 1 hour to a mixture of 47.3 g of 2-pentyl-1,2,3,4-tetrahydronaphthalene, 22.1 g of acetyl chloride and 380 ml of absolute dichloromethane, the yellow-brown mixture is boiled under reflux for 3 hours, left to stand overnight and then poured into a mixture of 500 ml of ice/water and 165 ml of concentrated hydrochloric acid. The organic layer is separated, the aqueous phase is extracted twice more with dichloromethane, the organic phases are washed with 230 ml of 3 N sodium hydroxide and with water, dried over sodium sulfate and the solvent is removed in vacuo. There are obtained 57.8 g of a mixture of 2-pentyl-6-acetyl-1,2,3,4-tetrahydronaphthalene and 2-pentyl-7-acetyl-1,2,3,4-tetrahydronaphthalene as a brownish liquid which is reacted directly.

(d) A solution of 54.6 g of the mixture of 2-pentyl-6-acetyl-1,2,3,4-tetrahydronaphthalene and 2-pentyl-7-acetyl-1,2,3,4-tetrahydronaphthalene in 450 ml of dioxane is warmed to 60° C. and allowed to flow while stirring over a 30 minute period into a solution of sodium hypobromite (prepared from 261 ml of 28% sodium hydroxide, 202 g of ice and 112 ml of water by the dropwise addition of 51.5 ml of bromine at 0° C. over a 35 minute period). The brownish mixture is subsequently warmed to 30° C., an exothermic reaction occuring with decolorization. The mixture is left to react for an additional 1 hour, the excess hypobromite is reduced by adding sodium hydrogen sulfite solution, 102 ml of concentrated hydrochloric acid are added thereto and the mixture is extracted with dichloromethane. After washing with water, drying with sodium sulfate and evaporating the solvent in vacuo, there are obtained 57.9 g of a crude mixture of 2-pentyl-1,2,3,4-tetrahydronaphthalene-6-carboxylic acid and 2-pentyl-1,2,3,4-tetrahydronaphthalene-7-carboxylic acid as a yellowish crystalline residue. The mixture of the two acids can be separated by repeated recrystallization from hexane, ethanol, isopropanol and the like. More successful, however, is the separation of the corresponding amides (prepared in accordance with Example 10) by recrystallization from suitable solvents, for example, acetone, and subsequent hydrolysis, for example, with potassium hydroxide in diethyleneglycol. 2-Pentyl-1,2,3,4-tetrahydronaphthalene-6-carboxamide melts at 166.4°–167.8° C. and 2-pentyl-1,2,3,4-tetrahydronaphthalene-7-carboxamide melts at 112.9°–123.5° C. The liquid crystalline 2-pentyl-1,2,3,4-tetrahydronaphthalene-6-carboxylic acid has a melting point of 122.9°–123.1° C. and a clearing point of 174.9°–177.6° C.; the 2-pentyl-1,2,3,4-tetrahydronaphthalene-7-carboxylic acid melts at 103.6°–105.5° C. and is not liquid crystalline.

The following compounds can be obtained in an analogous manner:

p-Cyanophenyl 2-heptyl-1,2,3,4-tetrahydro-6-naphthoate; m.p. 73.4° C., cl.p. 123.5° C.;
2-heptyl-1,2,3,4-tetrahydronaphthalene-6-carboxylic acid; m.p. 126.0°–126.5° C., cl.p. 168.4°–169.5° C.;
2-heptyl-1,2,3,4-tetrahydronaphthalene-7-carboxylic acid; m.p. 118.4°–119.0° C.;
2-heptyl-1,2,3,4-tetrahydronaphthalene-6-carboxamide; m.p. 133.5°–133.9° C.;
2-heptyl-1,2,3,4-tetrahydronaphthalene-7-carboxamide; m.p. 113.2°–113.7° C.

EXAMPLE 2

Preparation of p-ethoxy-phenyl-2-pentyl-1,2,3,4-tetrahydro-6-naphthoate

Analogously to Example 1, 6.16 g of 2-pentyl-1,2,3,4-tetrahydronaphthalene-6-carboxylic acid are converted into the acid chloride and this is reacted with 3.45 g of p-ethoxyphenol in 15 ml of absolute pyridine. There are obtained 8.9 g of crude p-ethoxyphenyl 2-pentyl-1,2,3,4-tetrahydro-6-naphthoate which, for purification, is chromatographed on 230 g of silica gel. Elution with toluene/hexane (1:1) and toluene/hexane (7:3) yields 8.8 g of substance which are recrystallized from acetone/hexane up to constant melting point and clearing point and dried in a high vacuum (0.01 mbar). There are obtained colorless crystals of p-ethoxy-phenyl 2-pentyl-1,2,3,4-tetrahydro-6-naphthalene; m.p. 95.4°–96.2° C., cl.p. 119.0°–119.4° C.

The following compound can be prepared in an analogous manner:

p-Ethoxyphenyl 2-heptyl-1,2,3,4-tetrahydro-6-naphthoate; m.p. 83.8° C., cl.p. 116° C.

EXAMPLE 3

Preparation of S-(p-ethoxyphenyl)2-pentyl-1,2,3,4-tetrahydro-thio-6-naphthoate

Analogously to Example 1, 2.0 g of 2-pentyl-1,2,3,4-tetrahydronaphthalene-6-carboxylic acid are converted with 20 ml of thionyl chloride into the acid chloride and this is reacted with 1.234 g of p-ethoxy-thiophenol in 5 ml of absolute pyridine. There are obtained 2.9 g of crude S-(p-ethoxyphenyl) 2-pentyl-1,2,3,4-tetrahydro-thio-6-naphthoate which, for purification, is chromatographed on 95 g of silica gel. Elution with hexane/toluene and toluene yields 2.7 g of substance which is recrystallized from acetone/hexane up to constant melting point and clearing point and dried up to constant weight in a high vacuum (0.01 mbar). There are obtained colorless crystals of S-(p-ethoxyphenyl)2-pentyl-1,2,3,4-tetrahydro-thio-6-naphthoate; m.p. 82° C., cl.p. 145° C.

EXAMPLE 4

Preparation of p-butylphenyl 2-pentyl-1,2,3,4-tetrahydro-6-naphthoate

Analogously to Example 1, 2.0 g of 2-pentyl-1,2,3,4-tetrahydronaphthalene-6-carboxylic acid are converted into the acid chloride and this is reacted with 1.202 g of p-butylphenol in 5 ml of absolute pyridine. There are obtained 3.0 g of crude p-butylphenyl 2-pentyl-1,2,3,4-tetrahydro-6-naphthoate for purification, is chromatographed on 95 g of silica gel. Elution with hexane/toluene (1:1) yields 2.8 g of substance which is recrystallized from ether/hexane up to constant melting point and clearing point and dried up to constant weight in a high vacuum (0.01 mbar). There are obtained colorless crystals of p-butylphenyl 2-pentyl-1,2,3,4-tetrahydro-6-naphthoate; m.p. 48.1° C., cl.p. 80.7° C.

EXAMPLE 5

Preparation of 6-pentyl-trans-decalin-2-carboxylic acid p-cyanophenyl ester 1.893 g of 6-pentyl-trans-decalin-2-carboxylic acid are boiled at reflux for 2 hours with 15 ml of thionyl chloride while excluding moisture. After removing the excess thionyl chloride in vacuo, the acid chloride is obtained as a brownish liquid.

The acid chloride, diluted with 10 ml of absolute benzene, is added dropwise while stirring at 3°–7° C. to a solution, cooled to 3° C., of 0.893 g of p-cyanophenol in 7.5 ml of absolute pyridine, the mixture is warmed at 50°–55° C. for 3.5 hours and left to stand at room temperature overnight. The mixture is then poured into a mixture of 15 g of ice and 15 ml of hydrochloric acid (1:1), exhaustively extracted with ether and the organic phases are washed once with 11.5 ml of ice-cold 1 N sodium hydroxide and with water. The crystalline residue (2.6 g) of 6-pentyl-trans-decalin-2-carboxylic acid p-cyanophenyl ester obtained after drying with sodium sulfate and removing the solvent in vacuo is, for purification, chromatographed on 90 g of silica gel. Elution with hexane/toluene and toluene yields 2.5 g of substance which is recrystallized from hexane up to constant melting point and clearing point and dried up to constant weight in a high vacuum (0.01 mbar). There are obtained colorless crystals of 6-pentyl-trans-decalin-2-carboxylic acid p-cyanophenyl ester; m.p. 79.9° C., cl.p. 148.0° C.

The 6-pentyl-trans-decalin-2-carboxylic acid used as the starting material can be prepared as follows:

(a) A mixture of 84.1 g of 4-pentylcyclohexanone, 51.3 g of pyrrolidine, 120 ml of toluene and 0.62 g of p-toluenesulfonic acid is heated to boiling for 2 hours while connecting a water-separator and separating the pyrrolidine-containing water which forms. The residue containing the 4-pentyl-1-pyrrolidinyl-1-cyclohexene is first freed from excess toluene in vacuo and subsequently distilled in a high vacuum; b.p. 107°–113° C. (0.16 mbar), yellowish liquid.

(b) While stirring and gassing with nitrogen there are added dropwise to a mixture of 98.4 g of 4-pentyl-1-pyrrolidinyl-1-cyclohexene and 315 ml of absolute toluene within 1 hour 35.9 g of methyl vinyl ketone (temperature increase to 42° C.). The mixture is left to stand overnight and then boiled under reflux for 3 hours. There is added to the boiling mixture a solution of 19.6 g of anhydrous sodium acetate and 39.1 ml of glacial acetic acid in 39.1 ml of water and the mixture is boiled under reflux for an additional 8 hours. After cooling, the toluene layer is separated, the aqueous phases are extracted twice more with toluene and the organic phases are washed in sequence with water, 1 N hydrochloric acid, water, saturated sodium hydrogen carbonate solution and water and then dried over sodium sulfate. After removing the solvent in vacuo, there is obtained a mixture of 6-pentyl-octahydro-$\Delta^{1,9}$-naphthalen-2-one and 6-pentyl-octahydro-$\Delta^{9,10}$-naphthalene-2-one as a brown liquid (106 g). For purification, the mixture is distilled in a high vacuum. Yield: 69.4 g of a yellowish liquid; b.p. 127°–132° C. (0.22 mbar).

(c) A solution of 71.2 g of the aforementioned mixture of 6-pentyl-octahydro-$\Delta^{1,9}$-naphthalen-2-one and 6-pentyl-octahydro-$\Delta^{9,10}$-naphthalen-2-one in 450 ml of absolute ether is added dropwise while stirring to a solution of 17.2 g of lithium wire in 2 liters of liquid ammonia (dry ice condenser), the mixture is left to react for an additional 1 hour, diluted with 1 liter of absolute ether and there are added portionwise 113 g of ammonium chloride until decolorization occurs. The ammonia is allowed to evaporate at room temperature overnight, the mixture is cooled with ice and made Congo-acid with concentrated hydrochloric acid. After adding water and an additional amount of ether, the ether layer is separated, the aqueous phase is extracted twice more with ether, the organic phases are washed with water and dried over sodium sulfate. After removing the solvent in vacuo, there are obtained 69.4 g of a mixture of predominantly 6-pentyl-trans-decalin-2-one and 6-pentyl-cis-decalin-2-one as a brown liquid which is used in the crude state.

(d) A solution of 23.6 g of sodium cyanide in 54 ml of water is added while gassing with nitrogen to 69.4 g of the aforementioned mixture of 6-pentyl-trans-decalin-2-one and 6-pentyl-cis-decalin-2-one dissolved in 350 ml of ether. The mixture is cooled to 0° C. and there are added dropwise thereto while stirring over 2 hours 69.9 ml of 25% hydrochloric acid. Subsequently, the mixture is stirred at room temperature for an additional 1 hour, the organic phase is separated, the aqueous phase is extracted twice more with ether, the combined organic phases are washed with water and dried with sodium sulfate. The cyanohydrin mixture (75.6 g of a brown oil) obtained after removing the solvent in vacuo is used in the crude state.

(e) 75.6 g of the aforementioned crude cyanohydrin mixture are dissolved while stirring in 81 ml of absolute pyridine and 67 ml of absolute benzene, cooled to $-2°$ C., treated dropwise within 20 minutes with a mixture of 42.0 ml of phosphorus oxychloride and 53.4 ml of absolute pyridine and subsequently boiled under reflux for 4 hours. The precipitate originally formed dissolves upon warming, but again forms upon cooling overnight. The mixture is poured on to 375 g of ice, diluted with ether, the ether layer is separated and the aqueous phase is extracted twice more with ether. The ether phases are washed with water, dried over sodium sulfate and freed from solvent in vacuo. There are obtained 72.5 g of a dark brown oil which consists predominantly of 6-pentyl-trans-octahydro-$\Delta^1$-naphthalene-2-carbonitrile and 6-pentyl-trans-octahydro-$\Delta^2$-naphthalene-2-carbonitrile as well as, in addition, the corresponding 9.10-cis compounds. The mixture is used in the crude state.

(f) The foregoing nitrile mixture (72.5 g) is heated at 200° C. (bath temperature) for 6.5 hours while gassing with nitrogen with a hot solution of 35.1 g of potassium hydroxide in 355 ml of diethyleneglycol. After this time, the ammonia evolution is almost complete. The mixture is left to cool, the alkaline solution, diluted with 500 ml of water, is extracted three times with ether and the organic phases are back-washed twice with water. The 17.2 g of dark brown oil obtained after drying with sodium sulfate and evaporating the ether are discarded. The aqueous phases, including water washings, are made Congo-acid with 3 N sulfuric acid, a precipitate or a turbidity occurring. The mixture is exhaustively extracted with ether and the organic phases are washed with water and dried with sodium sulfate. After evaporating in vacuo, there are obtained 57.6 g of a brown, solid residue which consists predominantly of 6-pentyl-trans-octahydro-$\Delta^1$-naphthalene-2-carboxylic and 6-pentyl-trans-octahydro-$\Delta^2$-naphthalene-2-carboxylic acid as well as, in addition, the corresponding 9,10-cis compounds. For purification, this residue is dissolved in warm toluene and filtered through a column of 300 g of silica gel. Elution with toluene and toluene containing 1% or 2% acetone yields a total of 45.9 g of brownish, crystalline substance which is used directly.

(g) The aforementioned mixture of unsaturated acids (45.9 g) is dissolved while warming in 700 ml of rectified alcohol, cooled to room temperature and, after treatment with 4.3 g of palladium/carbon (5% palladium) shaken in a hydrogen atomsphere until the hydrogenation comes to a standstill (24 hours). Subsequently, the catalyst is removed by filtration and the solvent is evaporated in vacuo. There are obtained 45.9 g of a yellowish crystalline residue which consists predominantly of 6-pentyl-trans-decalin-2-carboxylic acid and, in addition, still contains the cis isomers. For purification, the residue is recrystallized several times from ether/hexane or hexane, the purification being followed by gas chromatography, melting point and clearing point. After sublimation in a high vacuum (0.01 mbar), there are obtained 13.7 g of pure liquid crystalline 6-pentyl-trans-decalin-2-carboxylic acid as colorless crystals; m.p. 113.5°–114.3° C., cl.p. 165.8°–167.1° C.

The following compounds can be obtained in an analogous manner:

6-Ethyl-trans-decalin-2-carboxylic acid p-cyano-phenyl ester; m.p. 62.9° C., cl.p. 122° C.;
6-propyl-trans-decalin-2-carboxylic acid p-cyano-phenyl ester; m.p. 79.9° C., cl.p. 147.6° C.;
6-heptyl-trans-decalin-2-carboxylic acid p-cyano-phenyl ester; m.p. 76.4° C., cl.p. 141° C. (monotropic smectic below 56.5° C.);
6-ethyl-trans-decalin-2-carboxylic acid; m.p. 113.0°–114.5° C., cl.p. 142.2°–142.9° C.;
6-propyl-trans-decalin-2-carboxylic acid; m.p. 123.7°–124.5° C.; cl.p. 165.0°–166.0° C.;
6-butyl-trans-decalin-2-carboxylic acid; m.p. 113.9°–114.6° C.; cl.p. 159.3°–162.0° C.;
6-heptyl-trans-decalin-2-carboxylic acid; m.p. 114.8° C., cl.p. 162.0° C.

EXAMPLE 6

Preparation of 6-pentyl-trans-decalin-2-carboxylic acid p-ethoxy-phenyl ester

Analogously to Example 5, 1.893 g of 6-pentyl-trans-decalin-2-carboxylic acid are converted into the acid chloride and this is reacted with 1.036 g of p-ethoxy-phenol in 7.5 ml of absolute pyridine. After the same reaction procedure and working-up as described in Example 5, there are obtained 2.6 g of crude, crystalline 6-pentyl-trans-decalin-2-carboxylic acid p-ethoxyphenyl ester which, for purification, is chromatographed on 90 g of silica gel. Elution with hexane/toluene (1:1) and toluene yields 2.5 g of substance which is recrystallized from acetone/hexane up to constant melting point and clearing point and dried to constant weight in a high vacuum (0.01 mbar). There is obtained 6-pentyl-trans-decalin-2-carboxylic acid p-ethoxy-pehnyl ester as colorless crystals; m.p. 90.0° C., cl.p. 142.6° C.

EXAMPLE 7

Preparation of 6-pentyl-trans-decalin-2-carboxylic acid p-ethylphenyl ester

Analogously to Example 5, 1.893 g of 6-pentyl-trans-decalin-2-carboxylic acid are converted into the acid chloride and this is reacted with 0.916 g of p-ethylphenol in 7.5 ml of absolute pyridine. After the same reaction procedure and working-up, there are obtained 2.5 g of crude, crystalline 6-pentyl-trans-decalin-2-carboxylic acid p-ethylphenyl ester which, for purification, is chromatographed on 90 g of silica gel. Elution with hexane/toluene (1:1) yields 2.3 g of substance which is recrystallized from ether/hexane and hexane up to constant melting point and clearing point and dried up to constant weight in a high vacuum (0.01 mbar). There is obtained 6-pentyl-trans-decalin-2-carboxylic acid p-ethylphenyl ester as colorless crystals; m.p. 54.1° C., cl. p. 95.4° C.

The following compounds can be prepared in an analogous manner:

6-Methyl-trans-decalin-2-carboxylic acid p-butyl-phenyl ester; m.p. 59.5° C., cl.p. 48.9° C. (monotropic);
6-ethyl-trans-decalin-2-carboxylic acid p-ethyl-phenyl ester; m.p. 56.4° C., cl.p. 57.5° C.;
6-propyl-trans-decalin-2-carboxylic acid p-ethyl-phenyl ester; m.p. 74.9°–75.4° C., cl.p. 88.0° C.;
6-butyl-trans-decalin-2-carboxylic acid p-ethyl-phenyl ester; m.p. 66.9° C., cl.p. 84.5° C.;
6-heptyl-trans-decalin-2-carboxylic acid p-ethyl-phenyl ester; m.p. 66.0° C.;
6-heptyl-trans-decalin-2-carboxylic acid p-butyl-phenyl ester; m.p. 56.4° C., cl.p. 94.8° C. (monotropic smectic below 54.4° C.).

EXAMPLE 8

Preparation of 6-pentyl-trans-decalin-2-carbonitrile 8.95 g of 6-pentyl-trans-decalin-2-carboxamide are suspended in 94 ml of absolute pyridine and treated while stirring with 12.94 g of benzenesulfonyl chloride. The solution, which becomes clear, is left to stand at room temperature overnight, then poured into a mixture of 190 g of ice and 180 ml of hydrochloric acid (1:1) and exhaustively extracted with ether. The ether solutions are washed neutral with water, dried over sodium sulfate and the solvent is removed by evaporation in vacuo. There are obtained 11.0 g of crude 6-pentyl-trans-decalin-2-carbonitrile as a yellowish oil which crystallizes later and which, for purification, is chromatographed on 200 g of silica gel. Elution with hexane/toluene mixtures containing 30%, 40% and 50% of toluene yield 8.1 g of substance which is recrystallized from hexane up to constant melting point and subsequently distilled in a high vacuum; b.p. 115°–120° C. (0.02 mbar). There is obtained 6-pentyl-trans-decalin-2-carbonitrile as colorless crystals; m.p. 41.9° C.

The 6-pentyl-trans-decalin-2-carboxamide used as the starting material can be prepared as follows:

31.0 g of the mother liquors acid obtained in Example 5, which still contains the cis isomer in addition to 6-pentyl-trans-decalin-2-carboxylic acid, are converted into the acid chloride with 133 ml of thionyl chloride analogously to Example 5. After removing the excess thionyl chloride, it is diluted with 100 ml of absolute dichloromethane and this solution is added dropwise while stirring and cooling to a solution of 465 ml of absolute dichloromethane which is saturated with ammonia gas. Ammonia gas is introduced for an additional 2.5 hours. The mixture is evaporated to dryness in vacuo, treated with 530 ml of water and 500 ml of ether and stirred at room temperature for 30 minutes. The precipitate is removed by filtration under suction, washed with water and ether and dried. There are obtained 8.9 g of 6-pentyl-trans-decalin-2-carboxamide which, for purification is recrystallized from dioxane and sublimed in a high vacuum (0.01 mbar); colorless crystals, m.p. 211.6°–212.7° C. From the ether solutions there are obtained by repeated recrystallization (control by gas chromatography) an additional, 1.1 g of the trans amide and by recrystallization of the mother liquors from ether the 6-pentyl-cis-decalin-2-carboxamide as colorless crystals (m.p. 126.7°–128.0° C.).

The following compounds can be obtained in an analogous manner:

6-Ethyl-trans-decalin-2-carbonitrile; m.p. 34.7° C.;
6-propyl-trans-decalin-2-carbonitrile; m.p. 63.8° C.;
6-ethyl-trans-decalin-2-carboxamide; m.p. 224.6°–225.0° C.;
6-propyl-trans-decalin-2-carboxamide; m.p. 225.0°–226.0° C.;
6-ethyl-cis-decalin-2-carboxamide; m.p. 129.5°–131.5° C.;
6-propyl-cis-decalin-2-carboxamide; m.p. 126.6°–127.1° C.

EXAMPLE 9

Preparation of 2,6-dipentyl-trans-decalin

A mixture of 3.478 g of 6-pentyl-2-valeryl-trans-decalin, 11.4 ml of absolute ethanol and 1.339 g of hydrazine hydrate is dissolved while warming and left to stand overnight. After adding 12.2 ml of diethyleneglycol and 1.8 g of potassium hydroxide, the mixture is heated under a descending condenser for 2 hours at 200° C. (bath temperature) and left at this temperature for 1.5 hours. The distillate and residue are combined, treated with 25 ml of water and extracted with ether. The organic phases are washed with water and dried over sodium sulfate. After evaporating the solvent in vacuo, there are obtained 3.35 g of crude 2,6-dipentyl-trans-decalin which, for purification, is chromatographed on 90 g of silica gel. Elution with hexane yields 1.74 g of substance which is distilled in a high vacuum at 145° C./0.03 mbar. There are obtained colorless crystals of 2,6-dipentyl-trans-decalin; m.p. 47.8° C.

The 6-pentyl-2-valeryl-trans-decalin used as the starting material can be prepared as follows:

A Grignard solution is prepared by the dropwise addition of a mixture of 2.890 g of n-butyl bromide and 3.5 ml of absolute ether to a suspension of 0.513 g of magnesium in 7 ml of absolute ether. After dissolution of the magnesium, there is added dropwise at 35°–37° C. while stirring a solution of 4.101 g of 6-pentyl-trans-decalin-2-carbonitrile, prepared according to Example 8, in 7 ml of absolute ether, the mixture is boiled under reflux for 7 hours and left to stand overnight. Then, there are added dropwise 3.326 g of methanol and, after stirring for 30 minutes, the precipitate formed is removed by filtration under suction and washed well with absolute ether. Subsequently, hydrogen chloride gas is introduced into the filtrate for 1 hour while cooling at 0° C. and the mixture is concentrated to dryness. There are obtained 6.9 g of imine hydrochloride of 6-pentyl-2-valeryl-trans-decalin as a brownish, turbid oil. This is warmed at 50° C. with 50 ml of water for 30 minutes, the 6-pentyl-2-valeryl-trans-decalin separating as an oil which later crystallizes. The mixture is extracted with ether, the organic phase is washed with water, dried over sodium sulfate and the solvent is removed in vacuo. There remain 5.3 g of brownish, crystallizing oil which, for purification, can be recrystallized, for example, from hexane. There are thus obtained colorless crystals of 6-pentyl-2-valeryl-trans-decalin; m.p. 47.0°–48.5° C.

The following compounds can be obtained in an analogous manner:

2-Ethyl-6-propyl-trans-decalin; b.p. 90° C./0.007 mbar;
2-ethyl-6-pentyl-trans-decalin; b.p. 110° C./0.007 mbar;
2-ethyl-6-heptyl-trans-decalin; b.p. 140° C./0.007 mbar;
6-ethyl-2-propionyl-trans-decalin; liquid;
6-ethyl-2-valeryl-trans-decalin; oily;
6-ethyl-2-heptanoyl-trans-decalin; crystalline.

EXAMPLE 10

Preparation of 2-pentyl-1,2,3,4-tetrahydronaphthalene-6-carbonitrile 2.605 g of 2-pentyl-1,2,3,4-tetrahydro-naphthalene-6-carboxamide are suspended in 40 ml of absolute pyridine and treated with 2.86 g of benzenesulfonyl chloride while stirring. The solution, which becomes clear, is left to stand at room temperature overnight, the poured into a mixture of 50 g of ice and 40 ml of concentrated hydrochloric acid and exhaustively extracted with dichloromethane. The organic phases are washed neutral with water, dried over sodium sulfate and the solvent is removed by evaporation in vacuo. There are obtained 2.390 g of crude 2-pentyl-1,2,3,4-tetrahydronaphthalene-6-carbonitrile as a yellowish oil which, for purification, is chromatographed on 90 g of silica gel. Elution with hexane/toluene (1:1) and toluene yields 2.35 g of a yellowish oil which crystallizes at −10° C. It is crystallized up to a constant melting point from a small amount of ethanol by cooling the solution to −10° C. and separating the mother liquor from the precipitated crystals, for example, by decantation, pipetting or filtration through a cooled filter. Subsequently, it is dried up to constant weight in a high vacuum (0.01 mbar). There are obtained colorless crystals, or a colorless oil, of 2-pentyl-1,2,3,4-tetrahydronaphthalene-6-carbonitrile; m.p. 18.2° C.

The 2-pentyl-1,2,3,4-tetrahydronaphthalene-6-carboxamide used as the starting material can be prepared as follows:

7.4 g of the 2-pentyl-1,2,3,4-tetrahydronaphthalene-6-carboxylic acid obtained according to Example 1 are converted into the acid chloride with 68 ml of thionyl chloride as described in Example 1. After removing the excess thionyl chloride, the acid chloride is diluted with 100 ml of dichloromethane and this solution is added dropwise while stirring and cooling to a solution of 200 ml of absolute dichloromethane which is saturated with ammonia gas. Additional ammonia gas is introduced for an additional 2 hours, the mixture is evaporated to dryness in vacuo, treated with 200 ml of water, shaken for 30 minutes, the precipitate is removed by filtration under suction, washed with water and dried. There are obtained 7.66 g of crude 2-pentyl-1,2,3,4-tetrahydronaphthalene-6-carboxamide which, for purification, is recrystallized from dioxane and sublimed in a high vacuum (0.01 mbar); colorless crystals; m.p. 166.4°–167.8° C.

The following compounds can be prepared in an analogous manner:

2-Heptyl-1,2,3,4-tetrahydronaphthalene-6-carbonitrile; m.p. 36.5° C.;
2-heptyl-1,2,3,4-tetrahydronaphthalene-6-carboxamide; 133.5°–133.9° C.

EXAMPLE 11

Preparation of 6-ethyl-trans-decalin-2-carboxylic acid trans-4-pentyl-1-cyclohexyl ester 2.10 g of 6-ethyl-trans-decalin-2-carboxylic acid, prepared according to Example 5, are dissolved in 30 ml of absolute methylene chloride and treated with a solution 1.87 g of 4-pentyl-trans-cyclohexanol in 20 ml of absolute methylene chloride. Subsequently, there are added 0.20 g of 4-(dimethylamino)pyridine and, after cooling to 5° C., while stirring 2.48 g of solid dicyclohexylcarbodiimide. Dicyclohexylurea begins to separate out after a short time. After 1 hour at 2° C. and 1.25 hours at room temperature, the precipitate is removed by filtration under suction and back-washed with methylene chloride and hexane. By evaporating the filtrate in vacuo, there are obtained 4.80 g of crude 6-ethyl-trans-decalin-2-carboxylic acid trans-4-pentyl-1-cyclohexyl ester which, for purification, is chromatographed on 90 g of silica gel. Elution with hexane/toluene (1:1) yields 3.22 g of substance which is recrystallized from hexane up to constant melting point and clearing point and dried up to constant weight in a high vacuum (0.01 mbar). There is obtained 6-ethyl-trans-decalin-2-carboxylic acid trans-4-pentyl-1-cyclohexyl ester as colorless crystals; m.p. 50.4° C., cl.p. 86.3° C.

The following compound can be prepared in an analogous manner:

6-Butyl-trans-decalin-2-carboxylic acid trans-4-pentyl-1-cyclohexyl ester; m.p. 62.2°–65.4° C.; cl.p. 109.3° C.

EXAMPLE 12

Preparation of 6-butyl-trans-decalin-2-carboxylic acid trans-4-cyano-1-cyclohexyl ester 0.952 g of 6-butyl-trans-decalin-2-carboxylic acid, prepared according to Example 5, is dissolved in 18 ml of absolute methylene chloride together with 0.500 g of trans-4-hydroxycyclohexane-carbonitrile and 0.081 g of 4-(dimethylamino)-pyridine and then 0.992 g of dicyclohexyl-carbodiimide is added to the cooled solution. Dicyclohexylurea begins to separate out after a short time. After 1 hour at 2° C. and 1.25 hours at room temperature, the precipitate is removed by filtration under suction and back-washed with methylene chloride and hexane. By evaporating the filtrate in vacuo, there are obtained 1.831 g of crude 6-butyl-trans-decalin-2-carboxylic acid trans-4-cyano-cyclohexyl ester which, for purification, is chromatographed on 50 g of silica gel. Elution with toluene and toluene/0.5% or 1% acetone yields 1.240 g of substance which is recrystallized from acetone/hexane up to constant melting point and clearing point and dried up to constant weight in a high vacuum (0.01 mbar). There is obtained 6-butyl-trans-decalin-2-carboxylic acid trans-4-cyano-1-cyclohexyl ester as colorless crystals; m.p. 103.3° C.

EXAMPLE 13

Preparation of 6-pentyl-trans-decalin-2-carboxylic acid anilide

In order to purify the crude 6-alkyl-trans-decalin-2-carboxylic acids obtained according to Example 5, the corresponding 6-alkyl-trans-decalin-2-carboxylic acid anilides can also advantageously be prepared:

3.144 g of crude 6-pentyl-trans-decalin-2-carboxylic acid ae converted into the acid chloride in a manner analogous to that described in Example 5. After removing the excess thionyl chloride in vacuo, the crude acid chloride is dissolved in 15 ml of absolute methylene chloride and added dropwise while stirring to a cooled solution of 2.56 g of aniline in 35 ml of absolute methylene chloride, a precipitate of aniline hydrochloride forming immediately. After being stirred at room temperature for 2.5 hours, the mixture is treated with 50 ml of water and exhaustively extracted with methylene chloride. The organic extracts are washed with water, dried over sodium sulfate and the solvent is removed in vacuo. The crystalline residue of crude 6-pentyl-trans-decalin-2-carboxylic acid anilide is, for example, recrystallized from ethanol up to constant melting point and disappearance of the impurities in the gas chromatogram. There is thus obtained pure colorless 6-pentyl-trans-decalin-2-carboxylic acid anilide; m.p. 177.9°–178.6° C.

The following compounds can be prepared in an analogous manner:

6-Methyl-trans-decalin-2-carboxylic acid anilide; m.p. 188.2°–189.4° C.;
6-ethyl-trans-decalin-2-carboxylic acid anilide; m.p. 189.4°–190.8° C.;
6-propyl-trans-decalin-2-carboxylic acid anilide; m.p. 194.5°–196.3° C.;
6-butyl-trans-decalin-2-carboxylic acid anilide; m.p. 185.7°–186.7° C.;
6-heptyl-trans-decalin-2-carboxylic acid anilide; m.p. 171.9°–173.0° C.

The anilides can be converted into the pure 6-alkyl-trans-decalin-2-carboxylic acids by hydrolysis, for example with potassium hydroxide in ethyleneglycol at boiling temperature and subsequent acidification.

We claim:

1. A compound of the formula

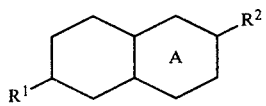

I wherein ring A is saturated or aromatic and a saturated ring A which may be present is trans-linked with the second ring; $R^1$ is straight-chain alkyl or alkoxy group containing 1 to 11 carbon atoms; $R^2$ is cyano, an ester group of the formula

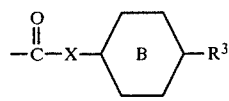

II wherein ring B is either aromatic, X is oxygen or sulfur and $R^3$ is cyano or straight-chain alkyl or alkoxy containing 1 to 10 carbon atoms, or ring B is trans-1,4-disubstituted cyclohexane, X is oxygen and $R^3$ is cyano or straight-chain alkyl containing 1 to 10 carbon atoms; and the total number of carbon atoms in the alkyl and/or alkoxy groups comprises at most 12.

2. A compound in accordance with claim 1, wherein ring A is saturated.

3. A compound in accordance with claim 2, wherein $R^2$ is an ester group of formula II.

4. A compound in accordance with claim 3, wherein ring B in the ester group of formula II is aromatic.

5. A compound in accordance with claim 4, wherein X in the ester group of formula II is oxygen.

6. A compound in accordance with claim 5, wherein $R^3$ in the ester group of formula II is cyano or straight-chain alkyl.

7. A compound in accordance with claim 2, wherein $R^2$ is cyano.

8. A compound in accordance with claim 1, wherein $R^2$ is cyano.

9. A compound in accordance with claim 1, 2, 3, 4, 5 or 7, wherein $R^1$ is straight-chain alkyl.

10. A compound, in accordance with claim 1, p-cyanophenyl 2-pentyl-1,2,3,4-tetrahydro-6-naphthoate.

11. A compound, in accordance with claim 1, p-ethoxy-phenyl 2-pentyl-1,2,3,4-tetrahydro-6-naphthoate.

12. A compound, in accordance with claim 1, 6-pentyl-trans-decalin-2-carboxylic acid p-cyanophenyl ester.

13. A compound, in accordance with claim 1, 6-pentyl-trans-decalin-2-carbonitrile.

14. A compound, in accordance with claim 1, 2-pentyl-1,2,3,4-tetrahydronaphthalene-6-carbonitrile.

15. A liquid crystal mixture containing at least two components, wherein at least one component is a compound of the formula

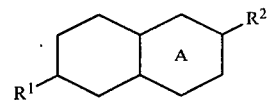

wherein ring A is saturated or aromatic and a saturated ring A which may be present is trans-linked with the second ring; $R^1$ is straight-chain alkyl or alkoxy group containing 1 to 11 carbon atoms; $R^2$ is cyano, straight-chain alkyl containing 1 to 11 carbon atoms, an ester group of the formula

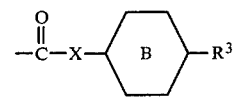

or, when ring A is saturated, additionally a straight-chain alkoxy group containing 1 to 11 carbon atoms; in the ester group of formula II ring B is either aromatic, X is oxygen or sulfur and $R^3$ is cyano or straight-chain alkyl or alkoxy containing 1 to 10 carbon atoms, or ring B is trans-1,4-di-substituted cyclohexane, X is oxygen and $R^3$ is cyano or straight-chain alkyl containing 1 to 10 carbon atoms; and the total number of carbon atoms in the alkyl and/or alkoxy groups comprises at most 12.

* * * * *